United States Patent [19]

Theodoropulos

[11] Patent Number: 4,789,742
[45] Date of Patent: Dec. 6, 1988

[54] ISOMALEIMIDE AND ISOPHTHALIMIDE DERIVATIVES OF CHROMOPHORS

[76] Inventor: Spyros Theodoropulos, 2964 Hickory St., Yorktown Heights, N.Y. 10598

[21] Appl. No.: 885,079

[22] Filed: Jul. 14, 1986

Related U.S. Application Data

[63] Continuation-in-part of Ser. No. 644,564, Aug. 27, 1984, Pat. No. 4,600,775.

[51] Int. Cl.$^4$ ............... C07C 103/153; C07C 103/24; C07D 265/38
[52] U.S. Cl. ..................... 544/69; 564/153; 564/156; 564/160; 435/4; 435/7; 435/29; 435/68; 436/94; 436/172; 530/402; 544/99; 544/103; 544/237; 549/214; 549/225; 556/411; 562/442; 562/450
[58] Field of Search ................... 544/99, 103, 237, 69; 549/225, 214; 260/377; 562/442, 450; 564/153, 156, 160; 435/4, 7, 29, 68; 530/402; 556/411; 436/94, 172

[56] References Cited

U.S. PATENT DOCUMENTS

| | | | |
|---|---|---|---|
| 2,998,429 | 8/1961 | Saures et al. | 549/321 |
| 4,179,466 | 12/1979 | Bollinger et al. | 564/156 X |
| 4,433,154 | 2/1984 | Hirai | 564/156 X |

Primary Examiner—Richard L. Raymond
Attorney, Agent, or Firm—Burgess, Ryan & Wayne

[57] ABSTRACT

Novel Isomaleimido and isophthalimido derivatives of chromophoric compounds are provided which are useful in analytic techniques for the detection and measurement of biological compounds such as bacteria, enzymes, hormones and the like.

11 Claims, No Drawings

ISOMALEIMIDE AND ISOPHTHALIMIDE DERIVATIVES OF CHROMOPHORS

BACKGROUND OF THE INVENTION

This application is a continuation-in-part of U.S. patent application Ser. No. 644,564 filed Aug. 27, 1984, now U.S. Pat. No. 4,600,775.

FIELD OF THE INVENTION

This invention relates in general to novel isomaleimides and isophthalimides. In one aspect, this invention relates to isomaleimides and isophthalimides which are derivatives of chromophoric compounds. In a further aspect, this invention relates to certain derivatives of chromophoric compounds which have the ability to react with a variety of organic substrates forming adducts which are useful in analytical techniques for the detection and measurement of biological compounds.

DESCRIPTION OF THE PRIOR ART

A variety of compounds have been reported in the literature as being useful in analytical techniques for the detection and measurement of biological properties and components of compounds of interest. Typical components include, among others, bacteria, viruses, enzymes, drugs, and hormones. For example, it is known that flouorescent groups such as fluorescein isothiocyanate can be introduced into certain specific compounds of biological interest. However, analytical techniques employing conjugates of fluorescein isothiocyanate undergo bleaching of the conjuage when exposed to ultraviolet light resulting in rapid loss of fluorescence.

Accordingly, one or more of the following objects can be achieved by the practice of this invention. It is an object of this invention to provide novel isomaleimido and isophthalimido derivatives of chromophors. Another object of this invention is to provide novel isomaleimido and isophthalimido derivatives of chromophors which may be readily coupled to compounds of clinical or biological interest. A further object of the present invention is to provide novel isomaleimides which will exhibit distinct fluorescence exitation and emission spectra, corresponding to that of the specific class of chromophors. It is also an object of the present invention to provide isomaleimido and isophthalimido derivatives of fluorescent molecules exhibiting superior stability over the native chromophors. A still further of this invention is to provide processes for the preparation of the novel chromophoric derivatives. Another object is to provide processes for the use of the derivatives for the detection and measurement of biological compounds. These and other will readily become apparent to those skilled in the art in light of the teachings herein set forth.

SUMMARY OF THE INVENTION

In its broad aspect, the present invention is directed to novel isomaleimido and isophthalimido derivatives of chromophoric compounds, processes for their preparation and use in the measurement and detection of biological compounds.

DETAILED DESCRIPTION OF THE INVENTION

The present invention is directed to novel isomaleimido and isophthalimido derivatives of chromophoric compounds. The isomaleimido or isophthalimido moiety allow the coupling of these chromophors to a variety of biological molecules of clinical interest.

The basic structure of the isomalemido and isophthalimido derivatives of chromphors which are prepared by the teachings of this invention are conveniently represented by the structural formulas I and II:

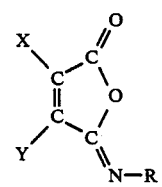

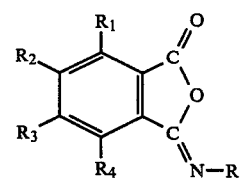

wherein R is an organic radical exhibiting chromophoric characteristics of analytical value; X and Y represent hydrogen, halogen, alkyl, aryl, alkoxy, aryloxy, nitro, amino, alkylamino, arylamino, mercapto, hydroxyl, hydroxyl, carboxy, nitro and sulfonic groups; and $R_1$–$R_4$ represent hydrogen, halogen, carboxy, alkoxy, aryloxy, alkyl, aryl, hydroxyl, amino, alkylamino, arylaino, nitro and sulfonic groups. In practice, the R groups contain from 1 to 18 carbon atoms and more preferably from about 1 to about 12 carbon atoms. Particularly preferred are those R groups which contain from 1 to 6 carbon atoms.

Typical examples of isomaleimido and isophthalimido chromophors are shown below:

Cresyl Violet-isomaleimide

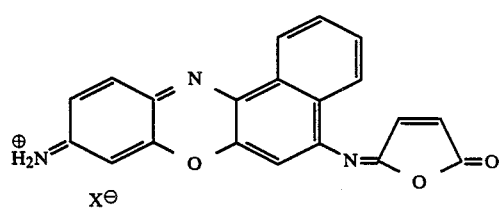

Fluorescein-isomaleimide

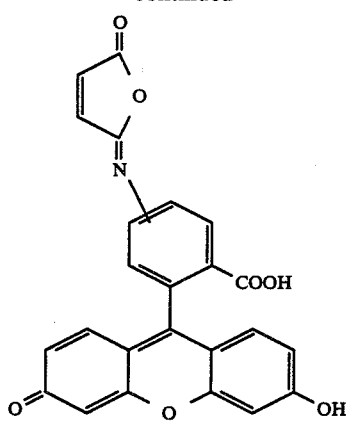

Fluorescein-isophthalimide

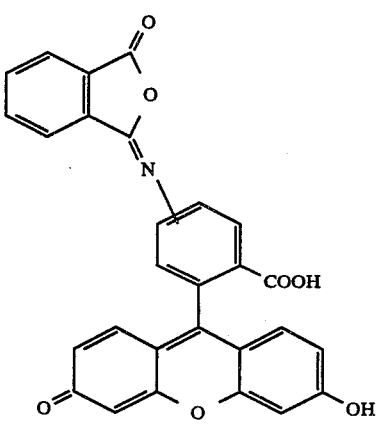

3-isomaleimido-luminol

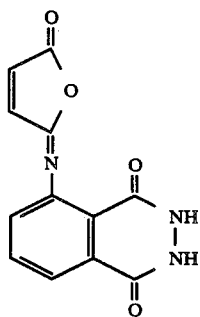

The isomaleimido and isophthalimido compounds herein above described are conveniently synthesized in two steps using known techniques. In practice, the reaction of a chromophor having an active amine group with maleic anhydride or phthalic anhydride afford the maleamic or phthalamic acid derivative. The process of the present invention can be illustrated by the synthesis of cresyl violet-maleamic acid and cresyl-violet phthalamic acid as shown in equations III and IV, respectively:

(III)

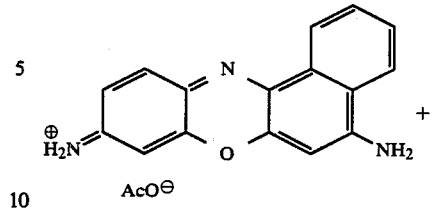

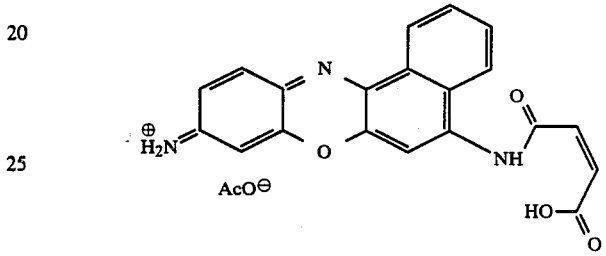

(IV)

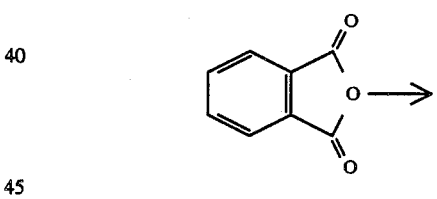

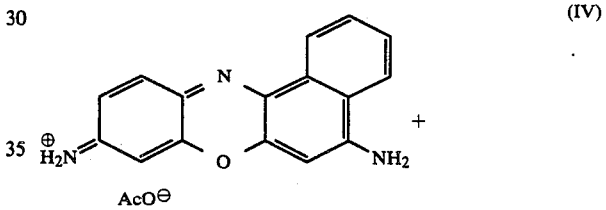

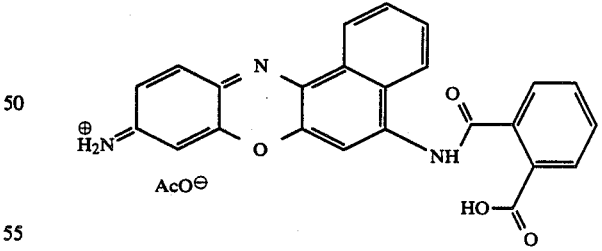

The reaction of the chromophors with maleic anhydride or phthalic anhydride is optionally performed in the presence of a solvent which is inert to the reactants and reaction products. Suitable solvents which can be employed include, among others, aliptic or aromatic chlorinated hydrocarbons, ethers, esters, pyridine, acetic acid, amides and the like. Particularly preferred for use as the solvent is acetic acid.

The process can be conducted at temperatures of from about 5° to about 150° C. with ambient temperatures being preferred.

The resulting maleamic or phthalamic acid derivative of the chromophors are thereafter dehydrated to provide the desired isomaleimido or isophthalimido derivative.

In general, the process by which the isomaleimides and isophthalimides of the present invention are prepared is by contacting the maleamic or the phthalamic acid having the general formula V and VI:

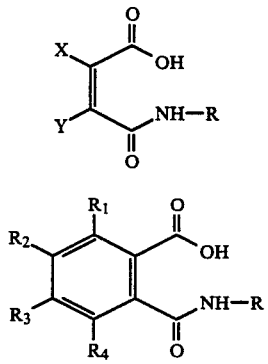

with an appropriate dehydrating agent. R in the above formulas is an organic chromophoric radical as herein before indicated; $R_1$-$R_4$ individually represent hydrogen, halogen, carboxyl, alkoxy or aryloxy; and X and Y individually represent hydrogen, halogen, carboxyl, alkyl, aryl, alkoxy, aryloxy, hydroxyl, mercapto, alkylamino, or arylamino groups.

Illustrative dehydrating agents which can be employed in the process of this invention include, among others, acide halides, chloroformates, trifluoroacetic anhydride or carbodiimides. The dehydration reaction is optionally performed in the presence of an organic solvent which is non-reactive with the starting materials or the desired product. Suitable organic solvents include, among others, the aromatic hydrocarbons such as benzene, toluene and the like; the halogenated aromatic hydrocarbons such as chlorobenzene and the like; cycloaliphatic hydrocarbons such as cyclohexane and the like; aliphatic hydrocarbons such as dichloromethane and the like; ethers such as diethyl ether, tetrahydrofuran, dioxane and the like; aliphatic ketones such as acetone; and dimethylformamide.

The temperature at which the reaction between the maleamic acid or the phthalamic acid and the dehydrating agent is conducted can vary over a wide range. Temperatures from as low as about −70° C. to the temperature just below that at which decomposition of the reactants or reaction product occurs can be employed.

The dehydration step of this invention can be illustrated by the following reaction:

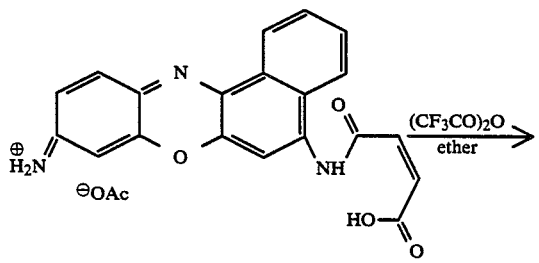

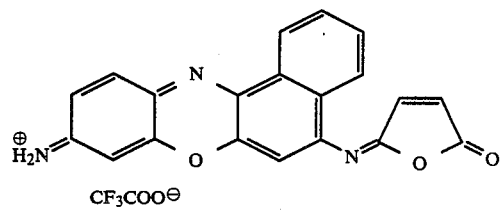

The desired derivative is then recovered by known techniques.

In another aspect of this invention the isomaleimides and isophthalimides of the general formula V and VI can react with an organic substrate containing a functional group having an active hydrogen. For example, conjugates of the chromophors of this invention and organic substrates can be conveniently represented by the formula:

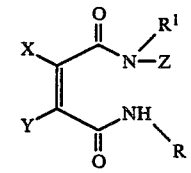

and

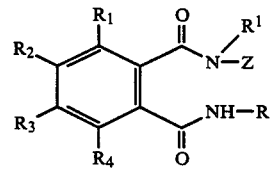

wherein R is a chromophor exhibiting fluorescence, luminescence, chemoluminescence or absorption of analytical value; Z is an organic substrate containing a functional group having an active hydrogen as hereinafter defined; $R_1$-$R_4$, and X and Y have the same values as previously indicated.

The chromophoric compounds of the present invention can be conveniently coupled to an inert matrix or organic substrate by known techniques to provide the conjugates of formulas VII and VIII above. For example, the chromophoric compounds can be coupled to a wide variety of biologically acceptable substrates which are normally employed in the detection and measurement of biological compounds. The only requirement of the matrix or substrate is that it contain one or more active sites through which coupling with the chromophoric derivative can be effected. In practice, such sites usualy contain an active hydrogen and include, but are not limited to, primary amines, secondary amines, hydroxyl groups, mercapto groups and the like. As indicated coupling of the chromphoric derivative to the matrix or substrate is effected by methods known to those skilled in the art to which this invention pertains.

It is therefore possible to form conjugates of the chromophoric derivatives with a wide variety of organic substrates, including, drugs, antigens, antibodies, haptens, peptides. proteins, amino acids, enzymes, and the like. A particularly preferred inert substrate which is widely used in the detection and measurement of biological compounds is the spherical beads employed in chromatographic techniques. For example, the derivatives of this invention can be conveniently enclosed in small beads such as those composed of polystyrene or other inert biological compositions.

The chromophoric derivatives of the present invention are therefore useful in a wide variety of areas as a biochemical tool for the detection and measurement of biological compounds. For example, the derivatives can be employed as conjugates with and inert matrix or organic substrate for use in antigen-antibody assays. Molecules, such as fluorescein or rhodamine are currently employed for fluorescence microscopy in indirect immunocytochemistry. Due to their improved stability, resistance to bleaching and the wide spread between excitation and emission the derivatives of the present invention are ideally suited for replacement of the fluorescein currently employed in fluorescent antibodies.

The derivatives of the present invention are also useful in conjunction with SDS gel electrophoresis for the study of peptide fragments from the cleavage of proteins. In such studies, chromatography and electrophoresis provide a 2-dimensional map or "fingerprint" diagnostic of a protein.

The chromophoric derivatives of the present invention are also useful as a replacement for radioactive tracers in automated electrophoresis processes such as those employed in determining the sequence of nucleic acids of genes. Newly available analytical instruments, such as the DNA sequencer, developed at the California Institute of Technology are currently in use to expedite gene mapping of strands of DNA. In the current version of these instruments a laser and fluorescent dyes replace the use of radioactive materials and result in markedly increased savings in the time needed to effect the mapping. In the DNA sequencer amino acids exposed to intense light cause the dye to glow. By computer analysis of the intensity and color, the identity of the nucleic acid base can be determined. The chromophoric derivatives of the present invention are particularly attractive for this application due to their stability in the presence of high intensity light such as the lasers employed in the DNA sequencer, and the distinct wide spread between the points of excitation and emission. Additionally, as previously indicated, the derivatives of the present invention are resistant to bleaching and hence are ideally suited for this application.

As previously indicated, the isomaleimido and isophthalimido compounds of this invention are bifunctional. The maleamic or phthalamic moieties act as ideal labeling agents due to their photochemical stability and the distinct characteristics exhibited by the same. Cresyl violet-maleamic, for example, shows an excitation at 480 nm and an emission at 580 nm, while the native chromophor exhibits an excitation at 600 nm and an emission at 630 nm. Fluorescein or fluorescein-isothiocyanate, a readily available chromphor, has been found to undergo rapid bleaching or loss of fluorescence when exposed to ultraviolet light. In contrast, the maleamic or phthalamic derivatives of this invention exhibit superior stability to ultraviolet light and undergo little or no bleaching. The isomaleimido and isophthalimido derivatives of the present invention are thus particularly useful in labeling biological compounds. It has also been observed that the compounds of the invention are also useful as staining materials for the staining of cells and as indicators.

The following examples illustrate to best mode presently contemplated for the practice of this invention.

EXAMPLE I

Preparation of N-(1-anthraquiniolyl)-maleamic acid

A mixture of 2.93 grams (0.01 mols) of 1-aminoanthraquinone and 1.3 grams of maleic anhydride in 5.0 milliliters of acetic acid was stirred at ambient temperature for 3 hours. The solid product was filtered off and washed with ether. There was obtained 3.5 grams of 1-anthraquinonemaleamic acid. I.R (nujol) showed bands at 5178 (maleamic); 6.0 (carbonyl); 6.15; 6.33; 7.45; and 7.80$\mu$.

EXAMPLE II

Preparation of 1-isomaleimidoanthraquinone 1.0 Gram of 1-anthraquinone-maleamic acid was suspended in 50 milliliters of diethyl ether. To this was added 3.0 milliters of trifluoroacetic anhydride and the mixture kept under nitrogen for 5 hours. The red maleamic acid was converted to the yellow 1-isomaleido anthraquinone. The product was filtered off and washed with ether. A total of 0.8 grams was isolated. I.R (nujol) showed bands of 5.57 (lactone); 5.90$\mu$ (imid); 5.95$\mu$ (carbonyl).

EXAMPLE III

Preparation of cresyl violet maleamic acid

A mixture of 321 mg (0.001 mols) of cresyl violet acetate and 150 mg excess of maleic anhydride in 5.0 milliliters of glacial acetic acid was stirred at ambient temperature for 24 hours. The reddish-brown solid product was filtered and washed with ether. 420 mg of the product was obtained. The product as characterized by infrared spectroscopy showed bands at (KBR) 2600 (carboxylic proton); 1685 (carboxylic); 1590 (aromatic); 1540; 1480; 1460; 1430; 1350; 1310; 1270; 1230; 11.95; 1150; and 1115 cm$^{-1}$.

EXAMPLE IV

Preparation of cresyl violet isomaleimide

420 Mg of cresyl violet-maleamic acid was suspended in 30 ml of diethylether. To this was added 1.0 milliliter of trifluoroacetic anhydride and the mixture left standing under an atmosphere of nitrogen for 15 hours. The solvent and the other volatiles were removed under reduced pressure. 390 Mg of cresyl violet-isomaleimide was obtained. I.R (smear) showed bands of 5.58 (lactone); 5.8 (CF$_3$COO); 6.05 (imid); 6.3; 6.45; 6.9; 7.6; 8.2; 8.6$\mu$.

Absorption $\lambda_{max}$ (in methanol) 512 nm.
Fluorescence $\lambda_{max}$ (methanol) 590 nm.

EXAMPLE V

Preparation of luminol-maleamic acid

A mixture of 1.77 grams (0.01 mol) of 3-amino phthalhydrazide and 1.5 grams of maleic anhydride in 10 milliliters of acetic acid was stirred at ambient temperature for 2 hours. The reddish product was filtered and washed with ether. 2.15 grams of luminol-maleamic acid was obtained. IR (KBR) showed bands at 3100; 3020; 2940; 2920; 2600; 1720; 1703; 1650; 1630; 1592; 1560; 1528; 1492; 1460; 1330; 1300; 1285; 1230; 1180 and 1120 cm$^{-1}$.

EXAMPLE VI

Preparation of Luminol-isomaleimide 1.0 Gram of luminol-maleamic acid was suspended in 50 ml of diethyl ether. To this was added 3.0 milliliters of trifluoroacetic anhydride and the mixture stirred under nitrogen for 2 hours. A yellow crystalline product was obtained which was filtered and washed with ether. The product was characterized by infrared spectroscopy and showed bands at (KBR) 1810 (lactone); 1770; 1728 (hydrazide carbonyl); 1678 (imid); 1635; 1605; 1590; 1525; 1330; and 1283 cm$^{-1}$.

EXAMPLE VII

Preparation of Fluorescein-5-maleamic acid

A mixture of 350 milligrams (0.001 mols) of 5-aminofluorescein and 300 milligrams (excess) of maleic anhydride were mixed in 5.0 milliliters of glacial acetic acid and the mixture was stirred at ambient temperature for 24 hours. The yellow product formed was filtered off and washed three times with diethyl ether. 420 Milligrams of fluorescein-maleamic acid was obtained. 1.R (KBR) showed bands at 2.55; 3.28; 3.38; 4.05; 5.85; 6.30; 6.52; 6.88; 6.90; 7.70; 8.34; 8.52; and 8.30$\mu$.

EXAMPLE VIII

Preparation of 5-isomaleimido-fluorescein 200 mg of fluorescein maleamic acid was suspended in 30 milliliters of diethylether. To this was added 1.0 milliliters of trifluoroacetic anhydride and the mixture was stirred under an atmosphere of nitrogen for one hour. The homogeneous solution was evaporated to dryness. 168 mg of isomaleimido-fluorescein was obtained. 1.R (smear) showed bands at 3.5 (COOH); 5.60 (lactone); 5.8 (carbonyl); 6.10 (imid); 6.2; 6.45; 6.68; 7.00; 8.30$\mu$.

EXAMPLE IX

Preparation of fluoresceinphthalamic acid

A mixture of 350 mg (0.001 mol) of 5-aminofluorescein and 200 mg of phthalic anhydride in 5 milliliters of glacial acetic acid was stirred at ambient temperature for 48 hours. The yellow reddish product was filtered and washed once with acetic acid and twice with diethyl ether. 460 Mg of fluorescein-phthalamic acid was obtained. I.R (KBR) showed bands at 3060; 3000; 1685; 1590; 1540; 1480; 1430; 1350; 1310; 1270; 1230; 1195; 1150; and 1115 cm$^{-1}$.

EXAMPLE X

Coupling of 5-Isomaleimide-fluorescein to Gamma globulin 6.4 nmoles of sheep gamma globulin dissolved in 2 milliters of 0.05M sodium carbonate buffer having a pH of 9.2, were added slowly with gentle stirring to 8.0 milliliters of a dimethylformamide solution containing 30.0 nmoles of 5-isomaleimide-fluorescein. The mixture was stirred at ambient temperatures for about 2 hours. The conjugate of 5-isomaleimido-fluorescein and sheep gamma globulin was purified by column chromatography using a Sephadex G-15 column equilibrated with PBS buffer having a pH of 7.0. The fraction containing the coupled product were monitored by ultraviolet absorption at 495 nm. The fraction containing the highest concentrations of the conjugate were pooled and lyphilized.

EXAMPLE XI

Labeling of Polystyrene Beads with Nile-Blue Maleamic Acid

Polystyrene beads (Dow diagnostic Lot Number 47864) having a diameter of ten microns were precipitated by centrifugation and the supernatent was removed by decantation. The beads were washed twice with ethanol and dried by passing astream of air. The beads were resuspended in in chloroform. To the chloroform suspension was added a drop of a dimethylformamide solution of nile blue maleamic acid and the mixture kept for 15 hours at ambient temperatures. The chloroform was removed by passing a stream of air and the beads washed with ethanol to remove excess of the Nile Blue-maleamic acid. The beads suspended in 1 percent sodium dodeacylsulfate in distilled water showed fluorescence excitation at 510 nm and emission at 580 nm.

Although the invention has been illustrated by the preceding examples, it is not to be construed as being limited to the materials employed therein, but rather, the invention encompasses the generic area as hereinbefore disclosed. Various modifications and embodiments thereof can be made without departing from the spirit and scope thereof.

What is claimed is:

1. A compound selected from the group consisting of:

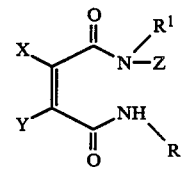

and

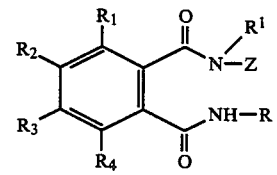

wherein R represents an organic chromophoric group exhibiting fluorescence, luminescense chemoluminesence or absorption properties; $R_1$, $R_2$, $R_3$ and $R_4$ individually represent hydrogen or halogen, or alkyl, aryl, hydroxyl, carboxyl, alkyl, or aryl-substituted or unsubstituted amino groups, nitro or sulfonic groups; X and Y represent hydrogen or halogen, or alkyl, aryl, alkoxy, aryloxy, carboxyl, hydroxyl, alkyl or aryl-substituted or unsubstituted amino groups, nitro or sulfonic groups, and Z represents an organic substrate free of chromophoric groups, and wherein

is derived from a primary or secondary amine.

2. The compound of claim 1 which is an N-substituted isomaleimide of the formula:

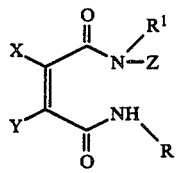

wherein R, S, X and Y are as indicated.

3. The compound of claim 1 which is an N-substituted isophthalimide of the formula:

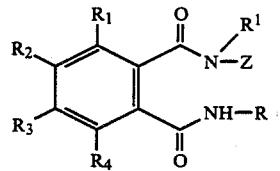

wherein R–R$_4$ and Z are as indicated.

4. The compound of claim 1 wherein said R group exhibits fluorescence properties.

5. The compound of claim 1 wherein said R group exhibits luminescence properties.

6. The compound of claim 1 wherein said R group exhibits chemoluminescence properties.

7. The compound of claim 1 wherein said R group exhibits absorption properties.

8. The compound of claim 1 wherein R is cresylviolet.

9. The compound of claim 1 wherein R is fluorescein.

10. The compound of claim 1 wherein R is nile blue.

11. The compound of claim 1 wherein R is luminol.

* * * * *